(12) United States Patent
Mou et al.

(10) Patent No.: US 11,187,215 B2
(45) Date of Patent: Nov. 30, 2021

(54) AIR QUALITY NOTIFICATION DEVICE

(71) Applicant: Microjet Technology Co., Ltd., Hsinchu (TW)

(72) Inventors: Hao-Jan Mou, Hsinchu (TW); Ta-Wei Hsueh, Hsinchu (TW); Li-Pang Mo, Hsinchu (TW); Shih-Chang Chen, Hsinchu (TW); Ching-Sung Lin, Hsinchu (TW); Chi-Feng Huang, Hsinchu (TW); Yung-Lung Han, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 244 days.

(21) Appl. No.: 16/026,472

(22) Filed: Jul. 3, 2018

(65) Prior Publication Data

US 2019/0035249 A1    Jan. 31, 2019

(30) Foreign Application Priority Data

Jul. 27, 2017    (TW) .................................. 106125344

(51) Int. Cl.
*F04B 17/05*    (2006.01)
*F24F 11/52*    (2018.01)
(Continued)

(52) U.S. Cl.
CPC .............. *F04B 17/05* (2013.01); *F04B 43/00* (2013.01); *F04B 43/046* (2013.01); *F24F 11/30* (2018.01);
(Continued)

(58) Field of Classification Search
CPC . G08B 21/12; F24F 11/52; F24F 11/30; F24F 2110/50; F24F 2221/12; G01N 1/24;
(Continued)

(56) References Cited

U.S. PATENT DOCUMENTS 6,165,347 A    12/2000 Warburton
2005/0223902 A1*   10/2005 Lovell ................ B01D 53/0415
96/134
(Continued)

FOREIGN PATENT DOCUMENTS

CN    101730284 A    6/2010
CN    102539626 A    7/2012
(Continued)

OTHER PUBLICATIONS

Cheng et al., "Design and fabrication of piezoelectric actuated valve micropump and its application in electronic cooling", Total 14 pages.

(Continued)

*Primary Examiner* — Nathaniel T Woodward
(74) *Attorney, Agent, or Firm* — Birch, Stewart, Kolasch & Birch, LLP

(57) ABSTRACT

An air quality notification device is disclosed. The air quality notification device includes an actuating and sensing module, a microprocessor, a first communication module and a power source. The actuating and sensing module includes a sensor and an actuating device. The actuating device is disposed near the sensor. The sensor senses air transmitted by the actuating device to generate air quality information. The microprocessor is electrically connected to the actuating and sensing module. The first communication module is electrically connected to the actuating and sensing module to receive and transmit the air quality information. The power source is electrically connected to the microprocessor.

21 Claims, 10 Drawing Sheets

(51) Int. Cl.
*G01N 1/24* (2006.01)
*G01N 1/22* (2006.01)
*F04B 43/00* (2006.01)
*F04B 43/04* (2006.01)
*F24F 11/30* (2018.01)
*G01N 1/00* (2006.01)
*G08B 21/12* (2006.01)
*G01N 15/02* (2006.01)
*G01N 15/06* (2006.01)
*G01N 15/00* (2006.01)
*F24F 110/50* (2018.01)
*G01N 33/00* (2006.01)

(52) U.S. Cl.
CPC ............ *F24F 11/52* (2018.01); *G01N 1/00* (2013.01); *G01N 1/2273* (2013.01); *G01N 1/24* (2013.01); *G08B 21/12* (2013.01); *F24F 2110/50* (2018.01); *F24F 2221/12* (2013.01); *G01N 15/02* (2013.01); *G01N 15/06* (2013.01); *G01N 33/0037* (2013.01); *G01N 33/0039* (2013.01); *G01N 33/0042* (2013.01); *G01N 33/0047* (2013.01); *G01N 33/0054* (2013.01); *G01N 2001/002* (2013.01); *G01N 2015/0046* (2013.01)

(58) Field of Classification Search
CPC ........ G01N 1/2273; G01N 1/00; G01N 15/02; G01N 15/06; G01N 2015/0046; G01N 33/0037; G01N 33/0039; G01N 33/0042; G01N 33/0047; G01N 33/0054; G01N 2001/002; F04B 43/00; F04B 43/046; F04B 17/05
See application file for complete search history.

(56) References Cited

U.S. PATENT DOCUMENTS

| | | | |
|---|---|---|---|
| 2009/0055102 | A1 | 2/2009 | Laufer et al. |
| 2009/0237261 | A1* | 9/2009 | Yokota ............... G08B 17/10 340/628 |
| 2014/0134053 | A1* | 5/2014 | Mayer ............... G01N 33/0009 422/83 |
| 2014/0292564 | A1 | 10/2014 | Park et al. |
| 2016/0076530 | A1* | 3/2016 | Chen ................. F04B 43/046 417/413.2 |
| 2016/0123622 | A1* | 5/2016 | Fu ................... F24F 11/0001 340/632 |
| 2019/0154551 | A1* | 5/2019 | Richter ............ F04B 43/046 |

FOREIGN PATENT DOCUMENTS

| | | |
|---|---|---|
| CN | 203310444 U | 11/2013 |
| CN | 205538890 U | 8/2016 |
| CN | 206038594 U | 3/2017 |
| CN | 206251549 U | 6/2017 |
| CN | 106970182 A | 7/2017 |
| EP | 2998582 A1 | 3/2016 |
| EP | 3023706 A1 | 5/2016 |
| FR | 2895518 A1 | 6/2007 |
| TW | M525446 U | 7/2016 |
| TW | M538545 U | 3/2017 |
| TW | M543870 U | 6/2017 |
| TW | M544653 U | 7/2017 |

OTHER PUBLICATIONS

Extended European Search Report, dated Dec. 3, 2018, for European Application No. 18181385.8.

* cited by examiner

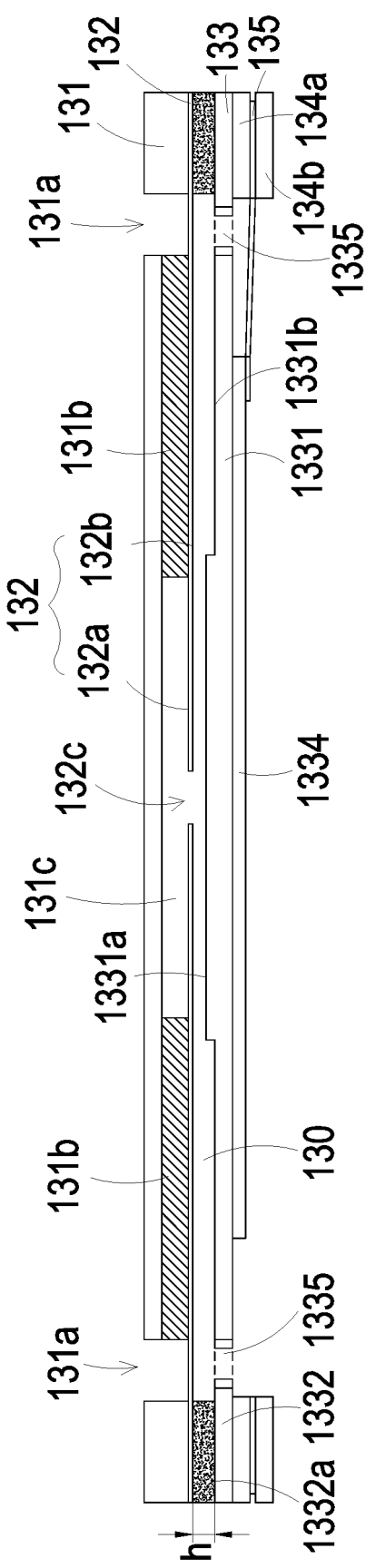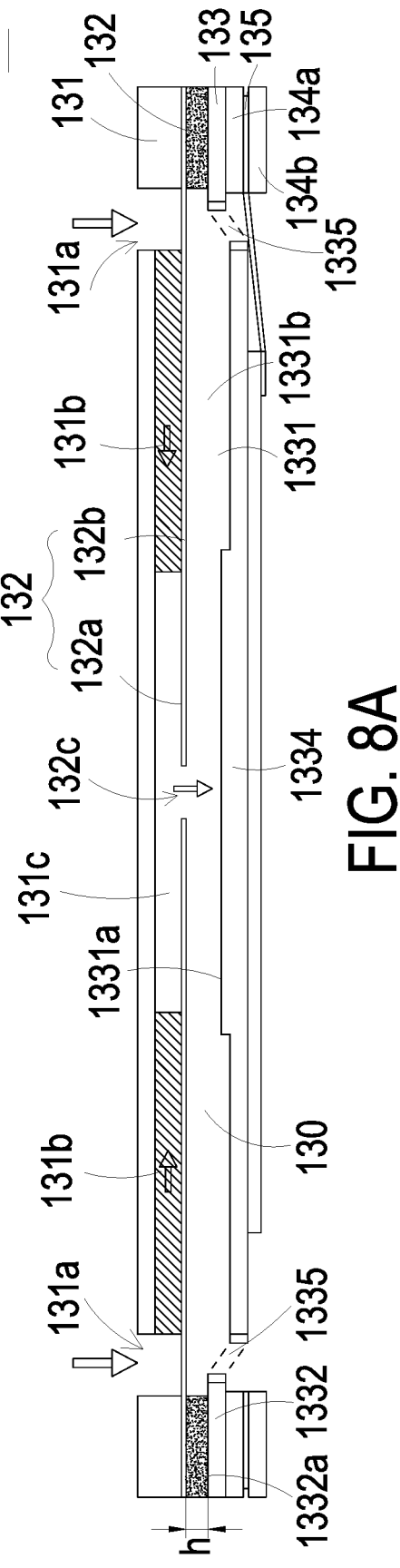

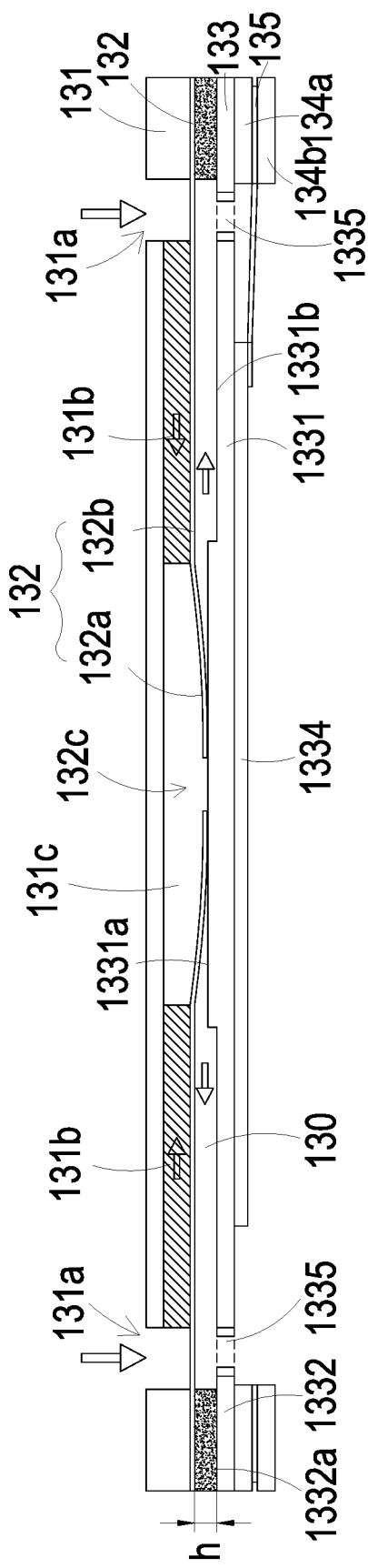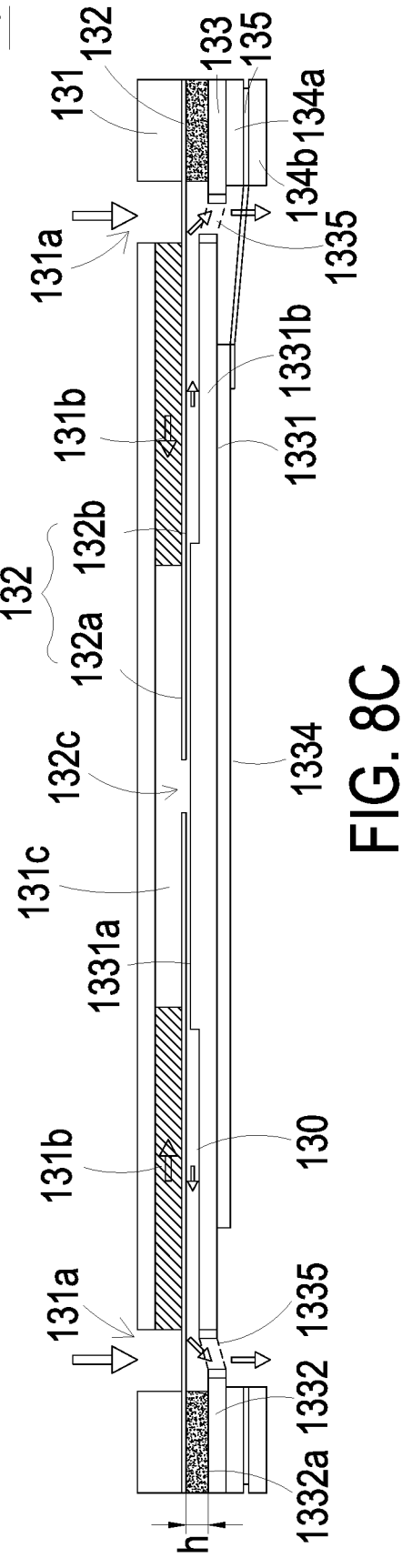

AIR QUALITY NOTIFICATION DEVICE

FIELD OF THE INVENTION

The present disclosure relates to an air quality notification device, and more particularly to an air quality notification device for reporting air quality in real time.

BACKGROUND OF THE INVENTION

Nowadays, people pay much attention to the air quality in the environment. For example, it is important to monitor carbon monoxide, carbon dioxide, volatile organic compounds (VOC), PM2.5, nitric oxide, sulfur monoxide, and so on. The exposure of these substances in the environment will cause human health problems or even harm the life. Therefore, it is important for every country to improve the air quality.

Generally, it is feasible to use an environmental sensor to monitor the air quality in the environment. If the environmental sensor is capable of immediately providing people with the monitored information relating to the environment for caution, it may help people escape or prevent from the injuries and influence on human health caused by the exposure of substances described above in the environment. In other words, the environmental sensor is suitably used for monitoring the ambient air in the environment.

Nowadays, a large-scale environmental monitoring base station is provided to monitor the ambient air quality. However, the large-scale environmental monitoring base station is only suitable for monitoring the ambient air quality near the environmental monitoring base station. If the large-scale environmental monitoring base station is used to monitor the air quality in a small area where the human activities exist (e.g., the indoor air quality and the ambient air surrounding us), the monitoring result is usually not accurately and quickly acquired. Consequently, the air quality cannot be effectively monitored everywhere and at any time.

Therefore, there is a need of providing an air quality notification device for monitoring the air quality everywhere and at any time, providing the air quality information in real time, and increasing the monitoring accuracy.

SUMMARY OF THE INVENTION

In accordance with an aspect of the present disclosure, an air quality notification device is provided. The air quality notification device includes an actuating and sensing module, a microprocessor, a first communication module and a power source. The actuating and sensing module includes a sensor and an actuating device. The actuating device is disposed near the sensor. The sensor senses air transmitted by the actuating device to generate air quality information. The microprocessor is electrically connected to the actuating and sensing module. The first communication module is electrically connected to the microprocessor to receive and transmit the air quality information. The power source is electrically connected to the microprocessor.

The above contents of the present disclosure will become more readily apparent to those ordinarily skilled in the art after reviewing the following detailed description and accompanying drawings, in which:

BRIEF DESCRIPTION OF THE DRAWINGS

FIG. 7 is a schematic cross-sectional view illustrating the fluid actuating device as shown in FIGS. 5A and 5B; and FIGS. 8A to 8E schematically illustrate the actions of the fluid actuating device of the actuating and sensing module according to the embodiment of the present disclosure.

DETAILED DESCRIPTION OF THE PREFERRED EMBODIMENT

Figure 1:
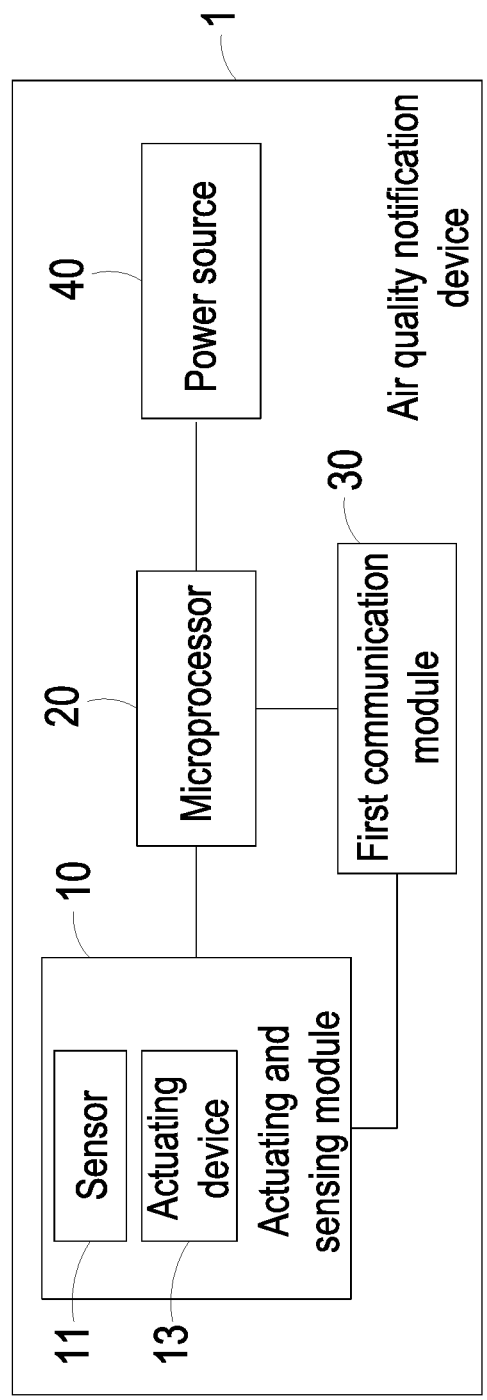
FIG. 1 schematically illustrates the architecture of an air quality notification device according to a first embodiment of the present disclosure.

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Please refer to FIGS. 1 to 4. The present discourse provides an air quality notification device 1 including at least one actuating and sensing module 10, at least one sensor 11, at least one actuating device 13, at least one air quality information, at least one microprocessor 20, at least one first connection module 30, and at least one power source 40. The number of the actuating and sensing module 10, the sensor 11, the actuating device 13, the air quality information, the microprocessor 20, the first connection module 30, and the power source 40 is exemplified by one for each in the following embodiments but not limited thereto. It is noted that each of the actuating and sensing module 10, the sensor 11, the actuating device 13, the air quality information, the microprocessor 20, the first connection module 30, and the power source 40 can also be provided in plural numbers.

FIG. 1 schematically illustrates the architecture of an air quality notification device according to a first embodiment of the present disclosure. As shown in FIG. 1, the air quality notification device 1 includes an actuating and sensing module 10, a microprocessor 20, a first communication module 30 and a power source 40. The actuating and sensing module 10 includes a sensor 11 and an actuating device 13. The actuating device 13 is disposed near the sensor 11. When the actuating device 13 is enabled, ambient air is inhaled into the air quality notification device 1 and transmitted to the sensor 11. After the ambient air is sensed by the sensor 11, air quality information around the air quality notification device 1 is generated. The microprocessor 20 is electrically connected to the actuating and sensing module 10 for enabling the actuating device 13 to operate. The first communication module 30 is electrically connected to the microprocessor 20 and the actuating and sensing module 10.

The air quality information is transmitted to the first communication module 30 and outputted from the air quality notification device 1 through the first communication module 30. The power source 40 is electrically connected to the microprocessor 20 and provides electric power to the air quality notification device 1.

An example of the power source 40 includes but is not limited to a graphene battery. Alternatively, the power source 40 includes a rechargeable battery.

In an embodiment, the microprocessor 20 is an application-specific integrated circuit (ASIC). In an embodiment, the microprocessor 20 and the first communication module 30 are integrated into a system on chip (SOC).

Figure 2:
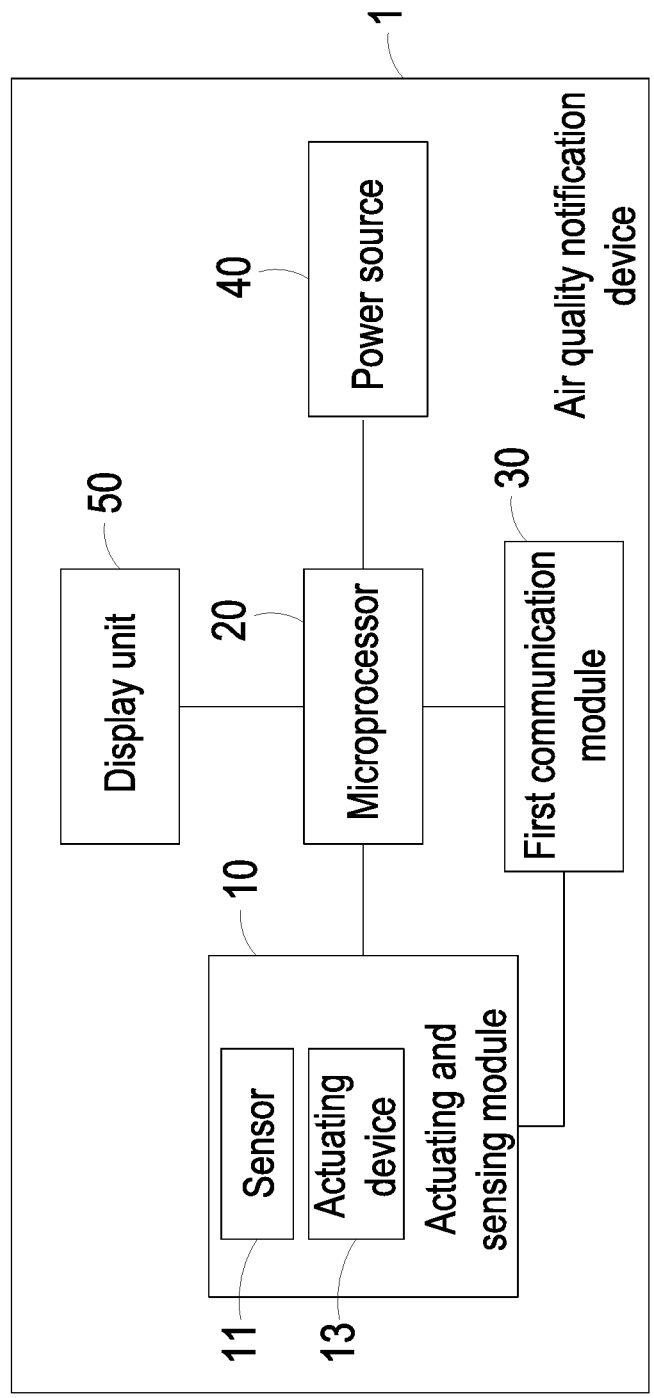
FIG. 2 schematically illustrates the architecture of an air quality notification device according to a second embodiment of the present disclosure.

FIG. 2 schematically illustrates the architecture of an air quality notification device according to a second embodiment of the present disclosure. As shown in FIG. 2, in comparison with the first embodiment, the air quality notification device 1 of this embodiment further includes a display unit 50. The air quality information is transmitted to the display unit 50 and shown on the display unit 50. Consequently, the current air quality can be confirmed by the user through the display unit 50.

Figure 3:
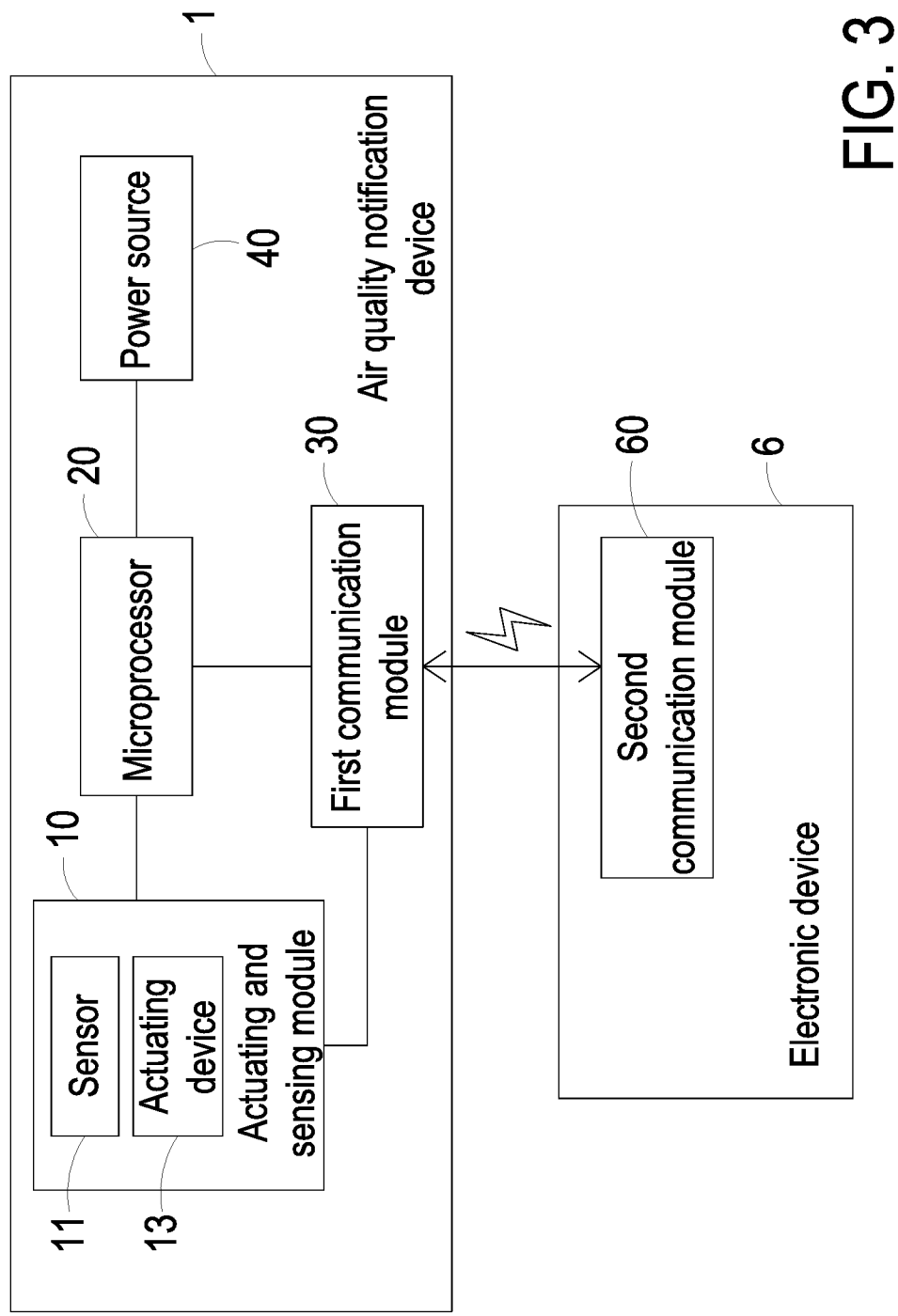
FIG. 3 schematically illustrates the architecture of an air quality notification device according to a third embodiment of the present disclosure.

FIG. 3 schematically illustrates the architecture of an air quality notification device according to a third embodiment of the present disclosure. As shown in FIG. 3, the air quality notification device 1 of this embodiment is in communication with a second communication module 60 of an electronic device 6 through the first communication module 30. The first communication module 30 and the second communication module 60 comply with the same specification. The air quality information is transmitted from the air quality notification device 1 to the second communication module 60 of the electronic device 6 through the first communication module 30. Consequently, the user can confirm the condition of the air quality through the electronic device 6 according to the air quality information.

In an embodiment, the first communication module 30 of the air quality notification device 1 and the second communication module 60 of the electronic device 6 may be wireless communication modules. The wireless communication module may perform a wireless communication process (for establishing a wireless transmission path) by using a Zigbee communication technology, a Z-wave communication technology, an RF communication technology, a Bluetooth communication technology, a Wi-Fi communication technology or an EnOcean communication technology. Alternatively, the first communication module 30 and the second communication module 60 may be wired communication modules. For example, the wired communication module has a USB port, an RS485 communication port, an RS232 communication port, a Modbus communication port or a KNX communication port for performing a wired communication process (for establishing a wired transmission path).

In an embodiment, the electronic device 6 may combine the air quality information with position information and transmits the combined information to a cloud device (not shown). Therefore, the air quality information at a location where the air quality notification device 1 is located can be confirmed by other user through the cloud device.

In an embodiment, the electronic device 6 may be a fixed-type electronic device (e.g., a desktop computer), a portable electronic device (e.g., a tablet computer, a notebook computer, or a mobile phone), or a wearable device (which may be an electronic device with display function, e.g., a watch, a smart bracelet or a smart glasses device).

For example, the air quality information includes the carbon monoxide concentration, the carbon dioxide concentration, the oxygen concentration, the fine suspended particle (PM2.5) concentration, the suspended particle (PM10) concentration, the ozone concentration, a volatile organic compound (VOC) concentration, the sulfur dioxide concentration, the nitrogen dioxide concentration, the humidity, the ammonia concentration, the methanol concentration, the alcohol concentration, or combinations thereof. Alternatively, the air quality information further includes the virus information, the bacterial information, the microbiological information, or combinations thereof.

Figure 4:
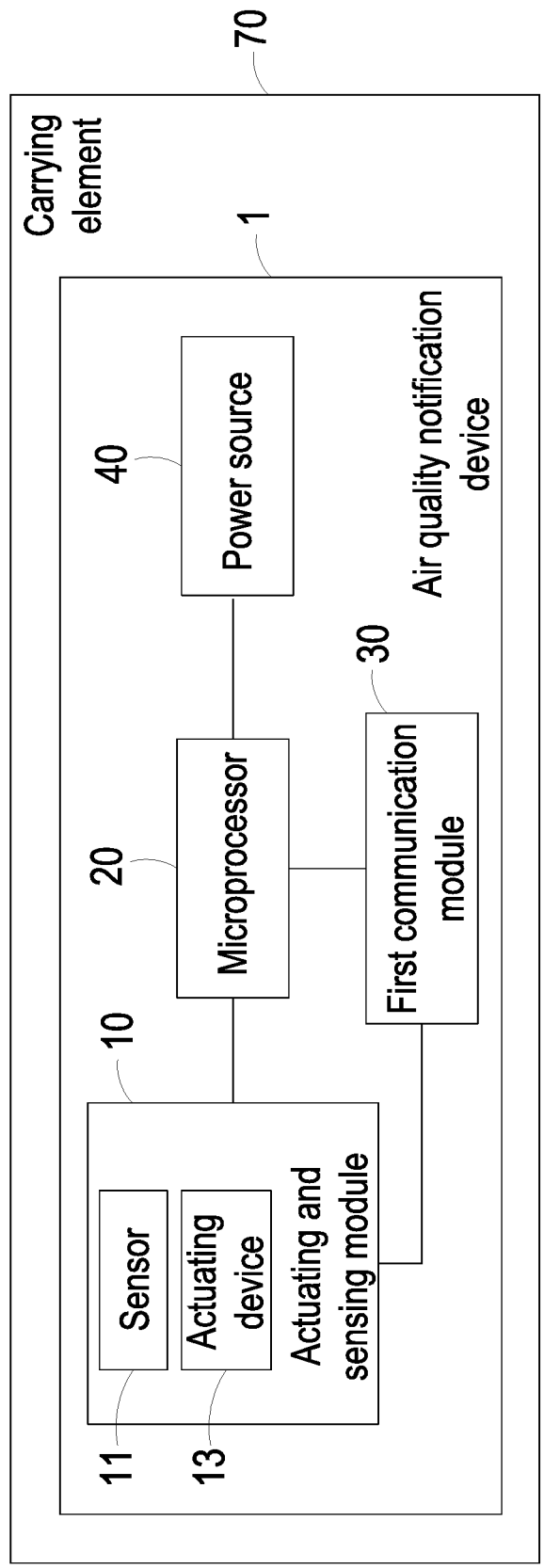
FIG. 4 schematically illustrates the architecture of an air quality notification device according to a fourth embodiment of the present disclosure.

Please refer to FIG. 4. In another embodiment, the air quality notification device 1 may be supported on a carrying element 70. For example, the carrying element 70 may be one selected from the group consisting of a hat, a glasses device, a chain, an earring, a headset, a clothing, a pocket, pants, a watch, a bracelet, a mobile phone, a mobile power bank, a mobile phone strap, a mobile phone case, a mask, a wallet, a bag, a shoe, a key ring and a belt. The carrying elements 70 described above are common accessories worn by the user when going out. Accordingly, the air quality notification device 1 installed on any common accessory (which is frequently used in daily life) is beneficial to increase applicability and aesthetically-pleasing appearance. In addition, it doesn't put any burden on the user, and may prevent the user from forgetting to take the air quality notification device 1 when going out. In some other embodiments, the air quality notification device 1 is embedded within the carrying element 70, but not limited thereto.

As mentioned above, the air quality information is acquired by the air quality notification device 1 and shown on the display unit 50 of the air quality notification device 1 or the display unit (not shown) of the electronic device 6. According to the air quality information, the user can learn whether the air quality is poor or the air quality is harmful to the human body. If the air quality is poor or the air quality is harmful to the human body, the user should leave the location or provide protective measures as soon as possible.

Figure 5A:
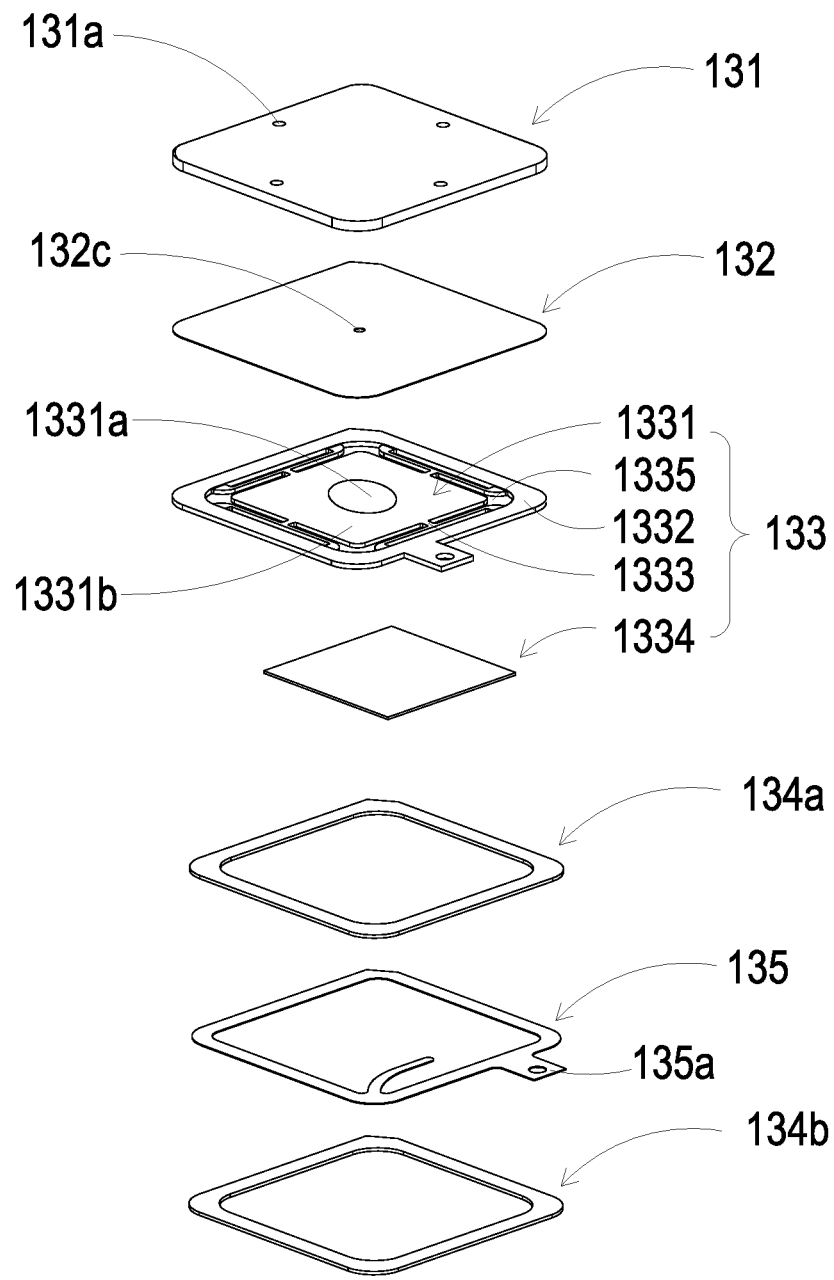
FIG. 5A is a schematic exploded view illustrating a fluid actuating device used in the actuating and sensing module of the present disclosure.
Figure 5B:
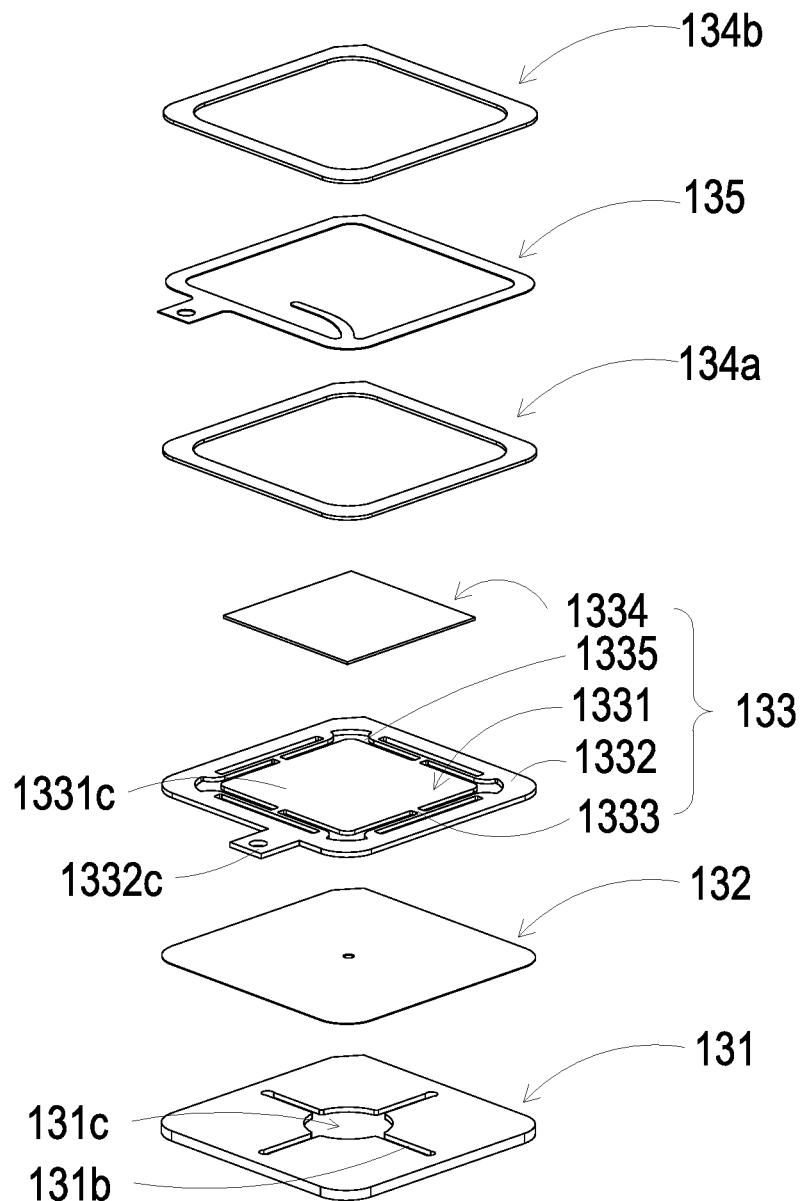
FIG. 5B is a schematic exploded view illustrating the fluid actuating device of FIG. 5A and taken along another viewpoint.

Please refer to FIGS. 5A and 5B. In an embodiment, the actuating device 13 is a fluid actuating device. The fluid actuating device 13 may be a driving structure of a piezoelectric pump or a driving structure of a micro-electromechanical system (MEMS) pump. Hereinafter, the actions of the fluid actuating device 13 of a piezoelectric pump will be described as follows.

Please refer to FIGS. 5A and 5B again. The fluid actuating device 13 includes a fluid inlet plate 131, a resonance plate 132, a piezoelectric actuator 133, a first insulation plate 134a, a conducting plate 135 and a second insulation plate 134b. The piezoelectric actuator 133 is aligned with the resonance plate 132. The fluid inlet plate 131, the resonance plate 132, the piezoelectric actuator 133, the first insulation plate 134a, the conducting plate 135 and the second insulation plate 134b are stacked on each other sequentially. After the above components are combined together, the cross-sectional view of the resulting structure of the fluid actuating device 13 is shown in FIG. 7.

The fluid inlet plate 131 includes at least one inlet 131a. Preferably but not exclusively, the fluid inlet plate 131 includes four inlets 131a. The inlets 131a run through the fluid inlet plate 131. In response to the action of the atmospheric pressure, the fluid can be introduced into the fluid actuating device 13 through the at least one inlet 131a. Moreover, at least one convergence channel 131b is formed on a first surface of the fluid inlet plate 131, and is in communication with the at least one inlet 131a on a second surface of the fluid inlet plate 131. Moreover, a central cavity 131c is located at the intersection of the convergence channels 131b. The central cavity 131c is in communication with the at least one convergence channel 131b such that the fluid from the at least one inlet 131a would be introduced into the at least one convergence channel 131b and is guided to the central cavity 131c. In this embodiment, the at least one inlet 131a, the at least one convergence channel 131b and the central cavity 131c of the fluid inlet plate 131 are integrally formed from a single structure. The central cavity 131c forms a convergence chamber for temporarily storing the fluid. In some embodiments, the fluid inlet plate 131 may be for example, made of stainless steel. Moreover, the depth of the convergence chamber defined by the central cavity 131c may be equal to the depth of the at least one convergence channel 131b. The resonance plate 132 is made of a flexible material. The resonance plate 132 has a central aperture 132c aligned with the central cavity 131c of the fluid inlet plate 131 which allows the fluid to be transferred therethrough. In other embodiments, the resonance plate 132 may be, for example, made of copper.

The piezoelectric actuator 133 includes a suspension plate 1331, an outer frame 1332, at least one bracket 1333 and a piezoelectric plate 1334. The piezoelectric plate 1334 is attached on a first surface 1331c of the suspension plate 1331. In response to an applied voltage, the piezoelectric plate 1334 is subjected to a deformation. When the piezoelectric plate 1334 is subjected to the deformation, it facilitates a bending vibration of the suspension plate 1331. The at least one bracket 1333 is connected between the suspension plate 1331 and the outer frame 1332, while the two ends of the bracket 1333 are connected with the outer frame 1332 and the suspension plate 1331 respectively that the bracket 1333 can elastically support the suspension plate 1331. At least one vacant space 1335 is formed between the bracket 1333, the suspension plate 1331 and the outer frame 1332. The at least one vacant space 1335 is in communication with a fluid channel for allowing the fluid to go through. The type of the suspension plate 1331 and the outer frame 1332 and the type and the number of the at least one bracket 1333 may be varied according to the practical requirements. The outer frame 1332 is arranged around the suspension plate 1331. Moreover, a conducting pin 1332c is protruded outwardly from the outer frame 1332 so as to be electrically connected to an external circuit (not shown).

Figure 6:
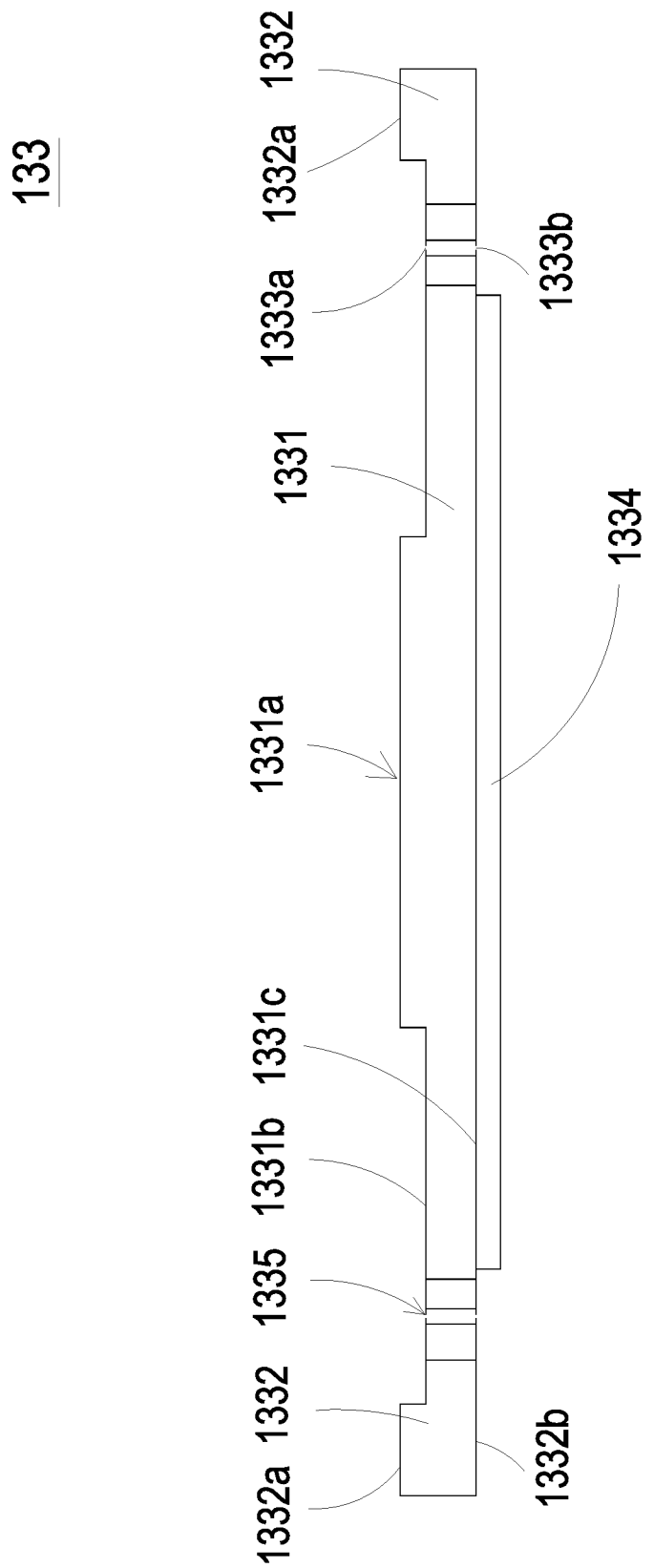
FIG. 6 is a schematic cross-sectional view illustrating the piezoelectric actuator of the fluid actuating device as shown in FIGS. 5A and 5B.

As shown in FIG. 6, the suspension plate 1331 has a bulge 1331a that makes the suspension plate 1331 a stepped structure. The bulge 1331a is formed on a second surface 1331b of the suspension plate 1331. The bulge 1331a may be a circular convex structure. A top surface of the bulge 1331a of the suspension plate 1331 is coplanar with a second surface 1332a of the outer frame 1332, while the second surface 1331b of the suspension plate 1331 is coplanar with a second surface 1333a of the bracket 1333. Moreover, there is a specific depth from the bulge 1331a of the suspension plate 1331 (or the second surface 1332a of the outer frame 1332) to the second surface 1331b of the suspension plate 1331 (or the second surface 1333a of the bracket 1333). A first surface 1331c of the suspension plate 1331, a first surface 1332b of the outer frame 1332 and a first surface 1333b of the bracket 1333 are coplanar with each other. The piezoelectric plate 1334 is attached on the first surface 1331c of the suspension plate 1331. In some other embodiments, the suspension plate 1331 may be a square plate structure with two flat surfaces, but the type of the suspension plate 1331 may be varied according to the practical requirements. In this embodiment, the suspension plate 1331, the at least one bracket 1333 and the outer frame 1332 may be integrally formed from a metal plate (e.g., a stainless steel plate). In an embodiment, the length of a side of the piezoelectric plate 1334 is smaller than the length of a side of the suspension plate 1331. In another embodiment, the length of a side of the piezoelectric plate 1334 is equal to the length of a side of the suspension plate 1331. Similarly, the piezoelectric plate 1334 is a square plate structure corresponding to the suspension plate 1331 in terms of design.

In this embodiment, the first insulation plate 134a, the conducting plate 135 and the second insulation plate 134b of the fluid actuating device 13 are stacked on each other sequentially and located under the piezoelectric actuator 133, as shown in FIG. 5A. The profiles of the first insulation plate 134a, the conducting plate 135 and the second insulation plate 134b substantially match the profile of the outer frame 1332 of the piezoelectric actuator 133. In some embodiments, the first insulation plate 134a and the second insulation plate 134b may be made of an insulating material (e.g. a plastic material) for providing insulating efficacy. In other embodiments, the conducting plate 135 may be made of an electrically conductive material (e.g. a metallic material) for providing electrically conducting efficacy. In this embodiment, the conducting plate 135 may have a conducting pin 135a disposed thereon so as to be electrically connected with an external circuit (not shown).

Please refer to FIG. 7. In an embodiment, the fluid inlet plate 131, the resonance plate 132, the piezoelectric actuator 133, the first insulation plate 134a, the conducting plate 135 and the second insulation plate 134b of the fluid actuating device 13 are stacked on each other sequentially. Moreover, there is a gap h between the resonance plate 132 and the outer frame 1332 of the piezoelectric actuator 133. In this embodiment, the gap h between the resonance plate 132 and the outer frame 1332 of the piezoelectric actuator 133 may be filled with a filler (e.g. a conductive adhesive) so that a depth from the resonance plate 132 to the bulge 1331a of the suspension plate 1331 of the piezoelectric actuator 133 can be maintained. The gap h ensures the proper distance between the resonance plate 132 and the bulge 1331a of the suspension plate 1331 of the piezoelectric actuator 133, so that the fluid can be transferred quickly, the contact interference is reduced and the generated noise is largely reduced. In some embodiments, alternatively, the height of the outer frame 1332 of the piezoelectric actuator 133 is increased, so that a gap is formed between the resonance plate 132 and the piezoelectric actuator 133.

Please refer to FIG. 5A, FIG. 5B and FIG. 7. After the fluid inlet plate 131, the resonance plate 132 and the piezoelectric actuator 133 are combined together, a movable part 132a and a fixed part 132b of the resonance plate 132 are defined. The movable part 132a is around the central aperture 132c. A convergence chamber for converging the fluid is defined by the movable part 132a of the resonance plate 132 and the fluid inlet plate 131 collaboratively. Moreover, a first chamber 130 is formed between the resonance plate 132 and the piezoelectric actuator 133 for temporarily storing the fluid. Through the central aperture 132c of the resonance plate 132, the first chamber 130 is in communication with the central cavity 131c of the fluid inlet plate 131. The peripheral regions of the first chamber 130 are in communication with the fluid channel through the vacant space 1335 between the brackets 1333 of the piezoelectric actuator 133.

Figure 8D:
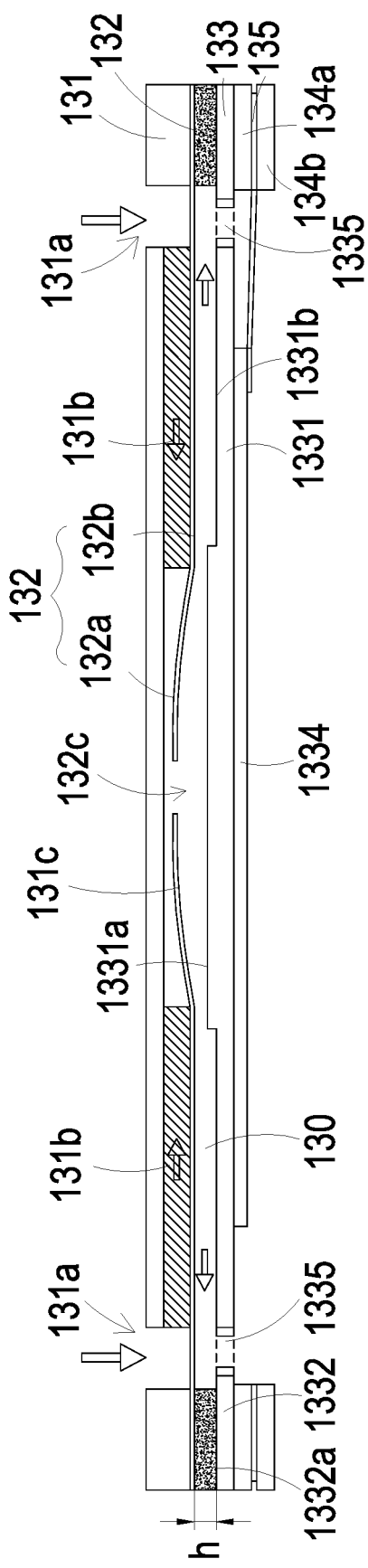
Figure 8E:
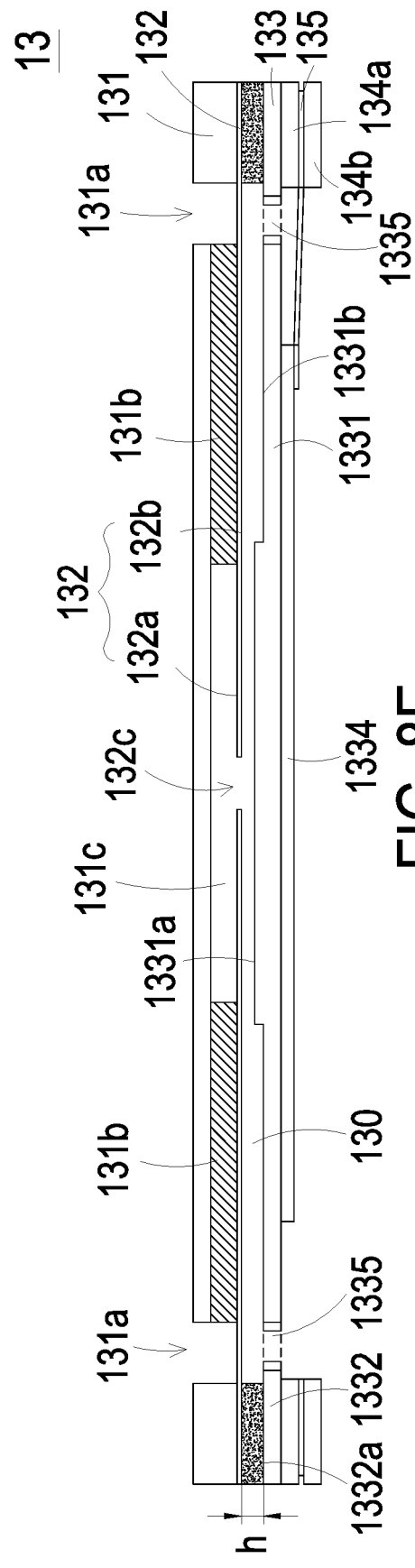

Please refer to FIG. 5A, FIG. 5B, FIG. 7 and FIGS. 8A to 8E. The actions of the fluid actuating device will be described as follows. When the fluid actuating device 13 is enabled, the piezoelectric actuator 133 vibrates along a vertical direction in a reciprocating manner by using the bracket 1333 as a fulcrum. Please refer to FIG. 8A, the piezoelectric actuator 133 vibrates downwardly in response to the applied voltage. Since the resonance plate 132 is light and thin, the resonance plate 132 vibrates along the vertical direction in the reciprocating manner in resonance with the piezoelectric actuator 133. More especially, a region of the resonance plate 132 spatially corresponding to the central cavity 131c of the fluid inlet plate 131 is also subjected to a bending deformation. The region of the resonance plate 132 corresponding to the central cavity 131c of the fluid inlet plate 131 is the movable part 132a of the resonance plate 132. When the piezoelectric actuator 133 deforms downwardly during vibration, the movable part 132a of the resonance plate 132 is subjected to the bending deformation because the movable part 132a of the resonance plate 132 is pushed by the fluid and vibrates in response to the piezoelectric actuator 133. In response to the downward deformation of the piezoelectric actuator 133 during the vibration, the fluid is fed into the at least one inlet 131a of the fluid inlet plate 131. Then, the fluid is transferred to the central cavity 131c of the fluid inlet plate 131 through the at least one convergence channel 131b. Then, the fluid is transferred through the central aperture 132c of the resonance plate 132 spatially corresponding to the central cavity 131c, and introduced downwardly into the first chamber 130. As the piezoelectric actuator 133 is enabled, the resonance of the resonance plate 132 occurs. Consequently, the resonance plate 132 vibrates along the vertical direction in the reciprocating manner. As shown in FIG. 8B, during the vibration of the movable part 132a of the resonance plate 132 at this stage, the movable part 132a moves down to contact and attach on the bulge 1331a of the suspension plate 1331 of the piezoelectric actuator 133, and a distance from the fixed part 132b of the resonance plate 132 to a region of the suspension plate 1331 except the bulge 1331a remains the same. Owing to the deformation of the resonance plate 132 described above, a middle communication space of the first chamber 130 is closed, and the volume of the first chamber 130 is compressed. Under this circumstance, the pressure gradient occurs to push the fluid in the first chamber 130 toward peripheral regions of the first chamber 130, and flowing downwardly through the vacant space 1335 of the piezoelectric actuator 133. As shown in FIG. 8C, the movable part 132a of the resonance plate 132 returns to its original position when the piezoelectric actuator 133 deforms upwardly during the vibration. Consequently, the volume of the first chamber 130 is continuously compressed to generate the pressure gradient which makes the fluid in the first chamber 130 continuously pushed toward peripheral regions. Meanwhile, the fluid is continuously fed into the at least one inlet 131a of the fluid inlet plate 131, and transferred to the central cavity 131c. Then, as shown in FIG. 8D, the resonance plate 132 moves upwardly, which is cause by the resonance of upward motion of the piezoelectric actuator 133. That is, the movable part 132a of the resonance plate 132 is also vibrated upwardly. Consequently, it decreases the current of the fluid from the at least one inlet 131a of the fluid inlet plate 131 into the central cavity 131c. At last, as shown in FIG. 8E, the movable part 132a of the resonance plate 132 has returned to its original position. As the embodiments described above, when the resonance plate 132 vibrates along the vertical direction in the reciprocating manner, the gap h between the resonance plate 132 and the piezoelectric actuator 133 is helpful to increase the maximum displacement along the vertical direction during the vibration. That is, the configuration of the gap h between the resonance plate 132 and the piezoelectric actuator 133 affects the amplitude of vibration of the resonance plate 132. Consequently, a pressure gradient is generated in the fluid channels of the fluid actuating device 13 to facilitate the fluid to flow at a high speed. Moreover, since there is an impedance difference between the feeding direction and the exiting direction, the fluid can be transmitted from the inlet side to the outlet side. Even if a gas pressure (which may impede the fluid flow) exists at the outlet side, the fluid actuating device 13 still has the capability of pushing the fluid to the fluid channel while achieving the silent efficacy. The steps of FIGS. 8A to 8E may be done repeatedly. Consequently, fluid circulation is generated in which the ambient fluid is transferred from the outside to the inside by the fluid actuating device 13.

According to an embodiment of the present disclosure, a power supply process for the air quality notification device 1 is described as follows. The power source 40 may be a rechargeable battery. The air quality notification device 1 includes a power supply device (not shown). The power supply device transfers energy to the power source 40 so that the power source 40 receives the energy to enable the sensor 11 to operate. The energy is a light energy, an electric energy, a magnetic energy, a sound energy or a chemical energy.

In an embodiment, the power supply device transfers the energy to the power source 40 through a wired transmission path. For example, the power supply device is a charger (not shown) which transfers the energy to the power source 40 through the wired transmission path. In another embodiment, the power supply device transfers the energy to the power source 40 through a wireless transmission path. For example, the power supply device is a charger with a wireless charging component (or an induction charging component) which transfers the energy to the power source 40 through the wireless transmission path. In another embodiment, the power supply device is a portable mobile device with wireless charging/discharging capability (e.g., a mobile phone). For example, the mobile phone has a wireless charging component (or an induction charging component) which transfers the energy to the power source 40 through the wireless transmission path.

From the above descriptions, the present disclosure provides an air quality notification device. The air quality notification device includes an actuating and sensing module, a microprocessor, a first communication module and a power source. Since the power source provides electric power to the air quality notification device, service of the air quality notification device is free of geographical restriction and it can be carried wherever the user chooses to go. The actuating and sensing module includes a sensor and an actuating device. The actuating device transmits the air to the sensor so that the sensor can sense the air rapidly and effectively and generate the air quality information. Since the first communication module is in communication with the electronic device, the air quality information is transmitted from the air quality notification device to the electronic device. The user can read the air quality information through the display unit of the electronic device. The air quality notification device of the present disclosure is capable of monitoring the air quality everywhere and at any time and immediately notification. In other words, the air quality notification device of the present disclosure is industrially valuable.

While the invention has been described in terms of what is presently considered to be the most practical and preferred embodiments, it is to be understood that the invention needs

What is claimed is:

1. An air quality notification device, comprising:
an actuating and sensing module comprising a sensor and an actuating device, wherein the actuating device is disposed near the sensor, the actuating device is in communication with a fluid channel having at least one inlet side and at least one outlet side for allowing an air to go through, and the sensor senses the air transmitted by the actuating device through the fluid channel to generate an air quality information;
a microprocessor electrically connected to the actuating and sensing module and disposed on at least one circuit isolated from the fluid channel;
a first communication module electrically connected to the actuating and sensing module to receive and transmit the air quality information; and
a power source electrically connected to the microprocessor and disposed on the at least one circuit,
wherein the actuating device has a central cavity defining a convergence chamber between at least one inlet and at least two outlets, when the at least one circuit obtains a driving power to enable the actuating device to compress the air in the fluid channel, the air is converged to the central cavity from the exterior of the actuating and sensing module through the at least one inlet, and a compressed air is transferred to the sensor through the at least two outlets.

2. The air quality notification device according to claim 1, wherein the air quality notification device further comprises a display unit for showing the air quality information thereon.

3. The air quality notification device according to claim 1, wherein the air quality notification device is in communication with a second communication module of an electronic device through the first communication module.

4. The air quality notification device according to claim 3, wherein the electronic device is a portable mobile device, the portable mobile device being one selected from the group consisting of a tablet computer, a notebook computer and a mobile phone.

5. The air quality notification device according to claim 3, wherein the electronic device is a wearable device, the wearable device being one selected from the group consisting of a watch, a smart bracelet and a smart glasses device.

6. The air quality notification device according to claim 1, wherein the air quality information is at least one selected from the group consisting of a carbon monoxide concentration, a carbon dioxide concentration, an oxygen concentration, a fine suspended particle (PM2.5) concentration, a suspended particle (PM10) concentration, an ozone concentration, a volatile organic compound (VOC) concentration, a sulfur dioxide concentration, a nitrogen dioxide concentration, a humidity, an ammonia concentration, a methanol concentration, an alcohol concentration, virus information, bacterial information, microbiological information and combinations thereof.

7. The air quality notification device according to claim 1, wherein the actuating device is a piezoelectric pump, and the piezoelectric pump comprises:
a fluid inlet plate having the at least one inlet, at least one convergence channel and the central cavity defining the convergence chamber, wherein the at least one inlet allows fluid to flow in, and wherein the convergence channel is disposed corresponding to the at least one inlet and guides the fluid from the at least one inlet into the convergence chamber defined by the central cavity;
a resonance plate having a central aperture and a movable part, wherein the central aperture is aligned with the convergence chamber, and the movable part surrounds the central aperture; and
a piezoelectric actuator aligned with the resonance plate, wherein a gap is formed between the resonance plate and the piezoelectric actuator to define a first chamber so that the fluid from the at least one inlet of the fluid inlet plate is converged to the central cavity along the at least one convergence channel and flows into the first chamber through the central aperture of the resonance plate when the piezoelectric actuator is enabled, whereby the fluid is further transferred through a resonance effect between the piezoelectric actuator and the movable part of the resonance plate.

8. The air quality notification device according to claim 7, wherein the piezoelectric actuator comprises:
a suspension plate having a first surface and an opposite second surface, wherein the suspension plate is permitted to undergo a bending vibration;
an outer frame arranged around the suspension plate;
at least one bracket connected between the suspension plate and the outer frame for elastically supporting the suspension plate; and
a piezoelectric plate, wherein a length of a side of the piezoelectric plate is smaller than or equal to a length of a side of the suspension plate, and the piezoelectric plate is attached on the first surface of the suspension plate, wherein when a voltage is applied to the piezoelectric plate, the suspension plate is driven to undergo the bending vibration.

9. The air quality notification device according to claim 1, wherein the first communication module is a wireless communication module or a wired communication module.

10. The air quality notification device according to claim 1, wherein the power source is a graphene battery.

11. An air quality notification device, installed on a carrying element, the air quality notification device comprising:
an actuating and sensing module comprising a sensor and an actuating device, wherein the actuating device is disposed near the sensor, the actuating device is in communication with a fluid channel having at least one inlet side and at least one outlet side for allowing an air to go through on the carrying element, and the sensor senses the air transmitted by the actuating device through the fluid channel to generate an air quality information;
a microprocessor electrically connected to the actuating and sensing module and disposed on at least one circuit isolated from the fluid channel;
a first communication module electrically connected to the actuating and sensing module to receive and transmit the air quality information; and
a power source electrically connected to the microprocessor and disposed on the at least one circuit,
wherein the actuating device has a central cavity defining a convergence chamber between at least one inlet and at least two outlets, when the at least one circuit obtains a driving power to enable the actuating device to compress the air in the fluid channel, the air is converged to the central cavity from the exterior of the actuating and sensing module through the at least one inlet, and a compressed air is transferred to the sensor through the at least two outlets.

12. The air quality notification device according to claim 11, wherein the carrying element is at least one selected from the group consisting of a hat, a glasses device, a chain, an earring, a headset, a clothing, a pocket, a part of pants, a watch, a bracelet, a mobile phone, a mobile power bank, a mobile phone strap, a mobile phone case, a mask, a wallet, a bag, a shoe, a key ring, a belt and combinations thereof.

13. The air quality notification device according to claim 11, wherein the air quality information is at least one selected from the group consisting of a carbon monoxide concentration, a carbon dioxide concentration, an oxygen concentration, a fine suspended particle (PM2.5) concentration, a suspended particle (PM10) concentration, an ozone concentration, a volatile organic compound (VOC) concentration, a sulfur dioxide concentration, a nitrogen dioxide concentration, a humidity, an ammonia concentration, a methanol concentration, an alcohol concentration, virus information, bacterial information, microbiological information and combinations thereof.

14. The air quality notification device according to claim 11, wherein the actuating device is a piezoelectric pump, and the piezoelectric pump comprises:
a fluid inlet plate having the at least one inlet, at least one convergence channel and the central cavity defining the convergence chamber, wherein the at least one inlet allows fluid to flow in, and wherein the convergence channel is disposed corresponding to the at least one inlet and guides the fluid from the at least one inlet into the convergence chamber defined by the central cavity;
a resonance plate having a central aperture and a movable part, wherein the central aperture is aligned with the convergence chamber, and the movable part surrounds the central aperture; and
a piezoelectric actuator aligned with the resonance plate, wherein a gap is formed between the resonance plate and the piezoelectric actuator to define a first chamber so that the fluid from the at least one inlet of the fluid inlet plate is converged to the central cavity along the at least one convergence channel and flows into the first chamber through the central aperture of the resonance plate when the piezoelectric actuator is enabled, whereby the fluid is further transferred through a resonance effect between the piezoelectric actuator and the movable part of the resonance plate.

15. The air quality notification device according to claim 14, wherein the piezoelectric actuator device comprises:
a suspension plate having a first surface and an opposite second surface, wherein the suspension plate is permitted to undergo a bending vibration;
an outer frame arranged around the suspension plate;
at least one bracket connected between the suspension plate and the outer frame for elastically supporting the suspension plate; and
a piezoelectric plate, wherein a length of a side of the piezoelectric plate is smaller than or equal to a length of a side of the suspension plate, and the piezoelectric plate is attached on the first surface of the suspension plate, wherein when a voltage is applied to the piezoelectric plate, the suspension plate is driven to undergo the bending vibration.

16. The air quality notification device according to claim 11, wherein the power source is a rechargeable battery.

17. The air quality notification device according to claim 11, wherein the air quality notification device further comprises a power supply device, and the power supply device transfers energy to the power source.

18. The air quality notification device according to claim 17, wherein the power supply device is a charger.

19. The air quality notification device according to claim 18, wherein the charger transfers the energy to the power source through a wired transmission path or a wireless transmission path.

20. The air quality notification device according to claim 17, wherein the power supply device is a portable mobile device with wireless charging/discharging capability.

21. An air quality notification device, comprising:
at least one actuating and sensing module comprising at least one sensor and at least one actuating device, wherein the actuating device is disposed near the sensor, the actuating device is in communication with a fluid channel having at least one inlet side and at least one outlet side for allowing an air to go through, and the sensor senses the air transmitted by the actuating device through the fluid channel to generate at least one air quality information;
at least one microprocessor electrically connected to the actuating and sensing module and disposed on at least one circuit isolated from the fluid channel;
at least one first communication module electrically connected to the actuating and sensing module to receive and transmit the air quality information; and
at least one power source electrically connected to the microprocessor and disposed on the at least one circuit to provide an electric power to enable the actuating device to drive the air to flow from the exterior of the actuating and sensing module into the fluid channel through the at least one inlet side, flow through the sensor and be discharged out through the at least one outlet side.

* * * * *